United States Patent [19]

Staebler

[11] Patent Number: 4,742,910

[45] Date of Patent: May 10, 1988

[54] NEEDLE SHEATH HOLDER

[76] Inventor: Charles R. Staebler, 11111 Shadywood, Brighton, Mich. 48116

[21] Appl. No.: 64,591

[22] Filed: Jun. 22, 1987

[51] Int. Cl.⁴ .......................... A61M 5/32; B65D 85/20
[52] U.S. Cl. ..................................... 206/365; 604/192; 604/263
[58] Field of Search ...................... 206/365, 366, 367; 604/192–198, 263

[56] References Cited

U.S. PATENT DOCUMENTS

| 3,783,997 | 1/1974  | Brown            | 206/365 |
| 3,820,652 | 6/1974  | Thackston        | 604/193 |
| 4,332,323 | 6/1982  | Reenstierna      | 206/365 |
| 4,454,944 | 6/1984  | Shillington et al. | 206/366 |
| 4,559,042 | 12/1985 | Votel            | 604/192 |
| 4,629,453 | 12/1986 | Cooper           | 604/192 |
| 4,654,034 | 3/1987  | Masters et al.   | 604/192 |

FOREIGN PATENT DOCUMENTS

| 0218169 | 1/1958 | Australia       | 604/193 |
| 0253426 | 5/1963 | Australia       | 206/365 |
| 0717777 | 9/1965 | Canada          | 206/365 |
| 8503006 | 7/1985 | PCT Int'l Appl. | 604/192 |
| 0178343 | 4/1922 | United Kingdom  | 604/192 |

Primary Examiner—Jimmy G. Foster
Attorney, Agent, or Firm—Harness, Dickey & Pierce

[57] ABSTRACT

A needle sheath holder consisting of a hollow barrel member having an open upper end and adapted to be held in the hand by a medical technologist during the sheathing and unsheathing of needles employed in extracting and injecting body fluids. A protective shield member of generally rectangular shape is mounted on the barrel member at a position to protect the hand of one holding the barrel during sheathing and unsheathing of a needle. Flexible gripper members at the open end of the barrel member are operable to frictionally engage a needle sheath inserted into the barrel member through the open end so as to retain the sheath in the barrel member.

5 Claims, 1 Drawing Sheet

NEEDLE SHEATH HOLDER

BACKGROUND AND SUMMARY OF THE INVENTION

This invention relates generally to the field of medical technology wherein sharp needles are used to withdraw and inject body fluids such as blood and medications and more particularly to a needle sheath holder which is usable to protect the technologist's fingers from the sharp end of the needle during fluid withdrawal and injection procedures.

Many extremely dangerous diseases and ailments are transmittable through the inadvertent and accidental needle prick of a technologist's skin. The object of this invention is to provide a needle sheath holder which can be hand held, set on a stand next to the patient or set in a test tube rack and which can be used by the technologist to prevent many inadvertent and accidental needle pricks during withdrawal and injection of body fluids.

The needle shaft holder of this invention comprises a hollow barrel member having an open upper end, a shield member on the barrel member spaced from the open end and gripper members in the open end operable to frictionally engage a needle sheath inserted into the barrel member through the open end so as to grip and retain the needle sheath in the barrel member. This enables the technologist to reinsert the needle into the needle sheath with the elimination of awkward handling procedures.

The sheath holder can be readily self-supported in a position in which the needle can be conveniently reinserted into the sheath and, in the event the needle sheath holder is hand held, the shield is of a size to protect the hand of the technologist that is holding the barrel member. As a result, inadvertent or awkward movements of the needle do not result in needle pricks of the technologist.

The shield member is generally rectangular to facilitate support of the needle sheath holder in an inclined position to accept a needle sheath and, in addition, the shield is of a size large enough to provide the necessary protection for the hand of the technologist.

The needle sheath holder of this invention thus provides for the immediate re-sheathing of the needle after use, thereby eliminating dangerous manipulations of an unsheathed needle.

The needle sheath holder is small enough to be carried in a pocket, is easily cleaned by washing in soap and water, and can readily be produced at low cost.

Further objects, features and advantages of the invention will become apparent from a consideration of the following description, the appended claims, and the accompanying drawing in which:

BRIEF DESCRIPTION OF THE DRAWINGS

With reference to the drawing, the needle sheath holder of this invention, indicated generally at 10, is illustrated in FIG. 3 as consisting of a hollow barrel member 12 having an open upper end 14 on which a conventional flexible plastic gripper assembly 16 is mounted. As shown in FIG. 3, the gripper assembly 16 has its outer surface formed with a plurality of radial slits or cuts 18 which divide the gripper assembly into a plurality of gripper members 20 of generally pie shape which can flex inwardly and outwardly relative to the barrel member 12.

The needle sheath holder 10 also includes a rectangular shield member 22 mounted on the barrel member 12 adjacent the open end 14. As shown in FIG. 4, the barrel member 12 is provided with a radially outwardly extending flange 24 against which one side of the shield member 22 is mounted. The opposite side of the shield member 22 is engaged by a mounting flange 26 on the gripper assembly 16.

Figure 1:
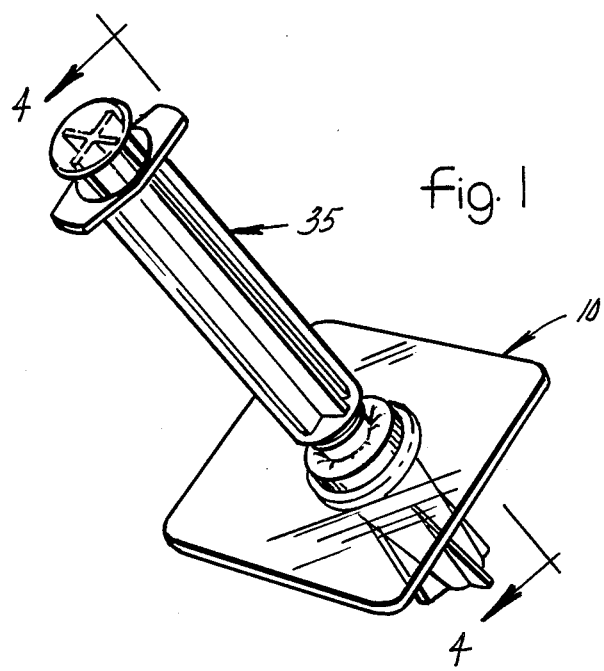
FIG. 1 is a perspective view of the needle sheath holder of this invention showing the holder in a position with a needle sheath and a hypodermic syringe extending into the barrel of the needle sheath holder.
Figure 2:
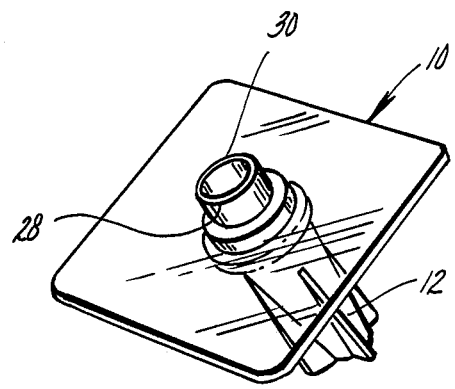
FIG. 2 is a perspective view of the needle sheath holder of this invention with a needle sheath retained therein.
Figure 3:
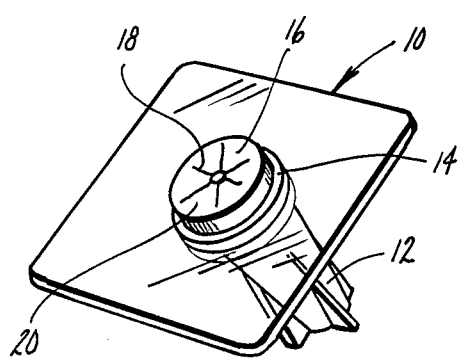
FIG. 3 is a perspective view of the needle sheath holder by itself.
Figure 4:
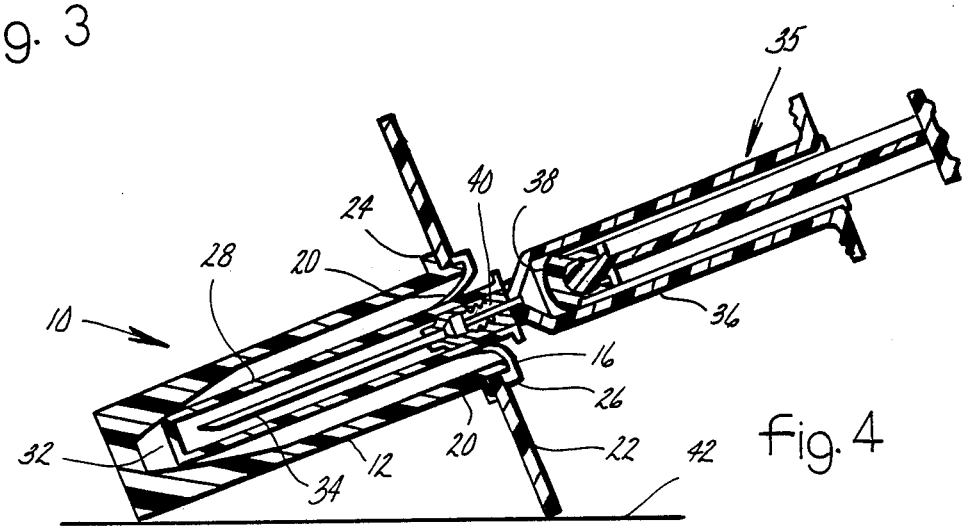
FIG. 4 is a longitudinal sectional view of the needle sheath holder of this invention in position supporting a hypodermic syringe and needle sheath as seen from substantially the line 4—4 in FIG. 1.

In use, the hollow barrel 22 is adapted to receive and house a needle sheath such as the one indicated at 28 in FIGS. 2 and 4. The needle sheath 28 is generally tubular in shape having an open outer end 30 and a closed inner end 32.

The needle sheath 28 is operable to enclose a variety of medical needles of the general type indicated at 34 in FIG. 4. Such needles can be part of a hypodermic syringe, such as the one illustrated at 35, for injecting fluid or a vacutainer for withdrawing fluid, mainly blood, or any other similar piece of medical equipment. The needle 34 is mounted on one end of a fluid containing cylinder 36 in which a plunger 38 is operable to discharge the fluid through the needle 34. The sheath 28 is frictionally retained on the cylindrical body 40 which supports the needle 34.

In the use of the needle sheath holder 10 of this invention, the barrel 12 is held in one hand while the medical technologist uses the other hand to manipulate a syringe assembly or vacutainer so that the needle sheath 28 is inserted into the barrel 12. During such insertion, the gripper members 20 are deflected inwardly into the barrel member 12, as shown in FIG. 4. The needle assembly is then withdrawn from the sheath leaving the needle sheath holder 10 in the barrel 12, as shown in FIG. 2, with the gripper members 20 infrictional engagement with the sheath 28.

The syringe 35 can then be manipulated for its intended purpose, namely either withdrawing body fluid or injecting fluid into the body and, when it is desired to return the needle 34 to its position within the sheath, the needle sheath holder 10 is held in one hand while the syringe 35 is manipulated with the other hand so as to insert the needle 34 into the sheath 28 and frictionally engage the open end 30 of the sheath with the cylindrical needle holder 40.

Importantly, during re-sheathing of the needle 34, the hand of the technologist holding the barrel 12 is protected by the shield member 22. This is because the shield member projects radially outwardly from the axis 44 of the barrel a distance at least equal to the diameter of the barrel member to thereby protect the user's hand if the needle 34 should miss the open end of the barrel 12. As a result, the technologist can not inadvertently stick the needle 34 into the holding hand. In the illustrated embodiment of the invention, the barrel member 12 is formed of a molded plastic material and the shield 22 is formed of a transparent plate of relatively rigid plastic material.

The rectangular shape of the shield 22 facilitates support of the needle sheath holder 10 in an inclined position on a flat surface 42, as shown in FIG. 4 so that the sheath 28 is in a position in which the needle 34 can be re-sheathed without the necessity for manually picking up the holder 12, if desired. In such position, a straight edge of the shield 22 and the lower end of the barrel 12 coact to firmly support the barrel 12 in an upwardly inclined position. The result is a needle sheath holder 10 which provides for the convenient re-sheathing of the needle 34 after use, thereby eliminating dangerous manipulations of an unsheathed needle which can result in injury to the needle user.

I claim:

1. For use with a medical needle assembly which includes a base and a needle mounted thereon, wherein a hollow needle sheath member is telescoped over said needle and frictionally engaged with said base when said needle is not being used as a conduit for fluid, a needle shaft holder comprising a hollow barrel member having an open upper end, a shield member on said barrel member spaced from said open end, and gripper members in said open end shaped to frictionally engage a needle sheath member inserted into said barrel member through said open end so as to grip and retain the needle sheath member in said barrel member.

2. The needle sheath holder according to claim 1 wherein said barrel member has a longitudinal axis and said shield is of a size to project radially outwardly from said axis a distance adequate to protect a human hand holding said barrel member.

3. The needle sheath holder according to claim 2 wherein said shield member has a straight edge which coacts with the lower end of said barrel member to enable said holder to be gravity supported on a flat surface with said axis extending upwardly at an inclined angle therefrom.

4. The needle sheath holder according to claim 3 wherein said shield member is rectangular in shape.

5. The needle sheath holder according to claim 1 wherein said gripper members are resilient pie shaped members supported on the open end of said barrel member and shaped to form a cover over the open end of said barrel member when the barrel member is empty.

* * * * *

UNITED STATES PATENT AND TRADEMARK OFFICE
CERTIFICATE OF CORRECTION

PATENT NO. : 4,742,910

DATED : May 10, 1988

INVENTOR(S) : Charles R. Staebler

It is certified that error appears in the above-identified patent and that said Letters Patent is hereby corrected as shown below:

Column 1, Line 22 "shaft" should be "sheath"

Claim 1, Column 3, Line 22 "shaft" should be "sheath"

Signed and Sealed this

Twenty-eighth Day of March, 1989

Attest:

DONALD J. QUIGG

Attesting Officer

Commissioner of Patents and Trademarks